Aug 6, 1974 G. MERRILL Plant Pat. 3,583
PEACH
Filed March 30, 1972
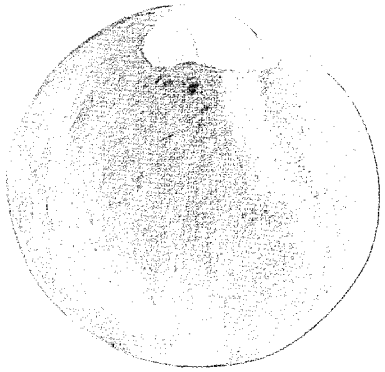
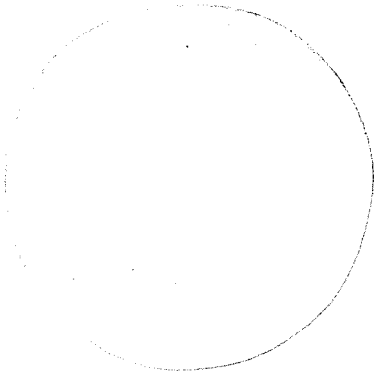
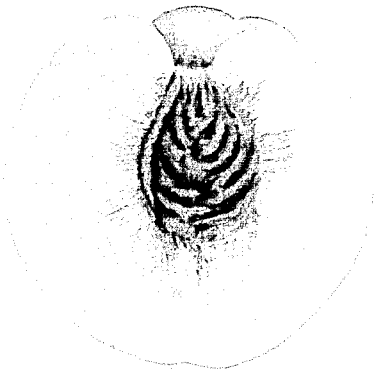

United States Patent Office

Plant Pat. 3,583
Patented Aug. 6, 1974

3,583

PEACH TREE

Grant Merrill, 416 N. Anderson Road,
Exeter, Calif. 93221

Filed Mar. 30, 1972, Ser. No. 239,830
Int. Cl. A01h 5/03
U.S. Cl. Plt.—43 1 Claim The present invention relates to a peach tree and more particularly to a new and distinct variety thereof broadly characterized by its very firm flesh and uniform texture and by a very bright undercolor of its skin which is covered with a red blush over 50% to nearly 100% of the surface of the fruit on mature trees, and by its extremely short pubescence.

The instant variety most nearly resembles O'Henry, U.S. Plant Pat. No. 2,964, but is an improvement thereon in ripening about three weeks earlier.

I originated this variety by planting seeds from fruit resulting from open pollinated O'Henry (P.P. 2,964) peach blossoms at Red Bluff, Tehama County, California. The instant variety (numbered E3–12 for my identification) was moved to Exeter, Tulare, County, Calif. as a seedling. The instant variety was asexually reproduced by grafting its scions into trees in test plots in various locations in Tulare County, Calif. and the resulting trees and fruit were identical. It was determined that the instant variety was worth commercial use.

The accompanying drawing is an oil painting of a characteristic fruit of the subject variety showing the shape and skin color, and by means of a fruit divided on its suture plane, showing the flesh and stone coloration and characteristics.

Referring now more specifically to the pomological characteristics of this new and distinct variety of peach tree, the following has been observed under the ecological conditions prevailing in Tulare County, Calif., and is an outline description thereof. All major color plate identifications are by reference to Maerz and Paul's Dictionary of Color, First Edition.

TREE

Size: medium, vigorous; may be pruned to vase shape.
Trunk: medium size, medium shaggy, gray.
Lenticels: medium in size and quantity.
Productivity: regular bearer.

LEAVES

Shape: lanceolate; tip, accuminate.
Size: medium; averaging 1½ to 1⅞ inches in width and 6 to 6¼ inches in length, medium thick.
Color: upper surface dark green, under surface light green.
Texture: smooth on young leaves, rugose on older leaves.
Margin: crenate.
Petiole: medium length.
Glands: reniform, stipules at the base of leaf dropping off early as the leaf grows.
Deciduous: yes.

FLOWERS

Buds: medium size, round, free, pubescent.
Blooms: showy, large.
Date of Bloom: medium late, about with O'Henry (P.P. 2,964).
Pollen: abundant.

FRUIT (described at maturity)

Season of ripening: late July in Tulare County, Calif.
Size: variable, generally medium; 2¼ to 2¾ inches in axial diameter, 2¼ to 2⅞ inches transverse in the suture plane, 2¼ to 2⅞ inches at right angle to suture plane.
Shape: generally globose.
Suture: a distinct shallow line extending from base to beyond and discontinuous at apex, with slight depression beyond the pistil point.
Ventral surface: rounded, slight lips usually unequal.
Cavity: oval, elongated in suture plane with suture showing strongly on one side, slightly on the other, generally ⅜ inches deep and ¾ inches wide, yellow with red markings.
Base: retuse.
Apex: mucronate.
Pistil Point: apical, short to very short.
Stem: ⅛ to ¼ inch long, ⅛ inch in diameter; frequently adhering slightly to flesh.
Flesh color: yellow, darkest near skin 9–I–2 to lightest toward stone 9–F–1 with red close to stone Afghan or Checkerberry red 5–L–6.
Amygdalin: moderate.
Juice: moderate.
Texture: uniform throughout, firm to moderately soft but meaty when fully ripe.
Fibers: few, fine, tender.
Ripens: evenly.
Flavor: delicate, distinct aroma.
Eating quality: best.

SKIN

Thickness: medium.
Texture: medium tender.
Tenacity to flesh: tenacious unless very ripe.
Pubescence: slight to almost none, very short.
Color: undercolor light yellow 9–L–4, red blush at stem end lightest 1–I–11 to Moroccan Red 5–K–11 to darkest Afghan or Checkerberry Red 5–L–6; red blush at apex end Moroccan red 5–K–11 to darker Mephisto red 3–K–10.

STONE

Color: light brown 12–L–10 to dark autumn brown 8–A–12.
Tenacity: completely free from the flesh.
Fibers: few, mostly short.
Size: medium to small.
Form: generally obovate to oval with small apical tip; base generally straight, sometimes oblique; hilum, oval; apex, accuminate to cuspidate; sides, generally unequal.
Surface: generally pitted and forrowed toward base, some at apex. Pits generally elongated, some round.
Ventral edge: thicker than dorsal edge with many fine furrows.
Dorsal edge: narrow with usually one deep groove from base to near apex.
Tendency to split: slight.

USE

Markets: local and distance shipment.
Eating: good quality.

Although the new variety of peach tree possesses the described characteristics under the growing conditions in Exeter, Tulare County, Calif., it is understood that variation of the usual magnitude in characteristics incident to the growing conditions, fertilization, pruning, and pest control is to be expected.

Having described and illustrated my new variety of peach tree, what is claimed is:

1. A new and distinct variety of peach substantially as described and illustrated which is characterized by its firm flesh and uniform texture, a very bright yellow undercolor of its skin with a bright red blush over 50% to 100% of its surface on mature trees, and short pubescence on the skin, which most closely resembles O'Henry peach plant (P.P. 2,964), its parent, but is an improvement thereon in ripening about three weeks earlier.

No references cited.

ROBERT E. BAGWILL, Primary Examiner